US010315662B2

(12) United States Patent
Terwilliger et al.

(10) Patent No.: US 10,315,662 B2
(45) Date of Patent: Jun. 11, 2019

(54) DETERMINING A DRIVER CONDITION USING A VEHICLE GATEWAY

(71) Applicant: Dell Products L.P., Round Rock, TX (US)

(72) Inventors: Kevin Terwilliger, Austin, TX (US); Andrew Tosh, Cedar Park, TX (US); Jefferson Walter Wirtz, Round Rock, TX (US); Rex Bryan, Round Rock, TX (US)

(73) Assignee: Dell Products L.P., Round Rock, TX (US)

( * ) Notice: Subject to any disclaimer, the term of this patent is extended or adjusted under 35 U.S.C. 154(b) by 0 days.

(21) Appl. No.: 15/286,534

(22) Filed: Oct. 5, 2016

(65) Prior Publication Data

US 2018/0093672 A1    Apr. 5, 2018

(51) Int. Cl.
| | |
|---|---|
| *G08B 23/00* | (2006.01) |
| *B60W 50/00* | (2006.01) |
| *H04W 88/16* | (2009.01) |
| *A61B 5/18* | (2006.01) |
| *G08B 21/06* | (2006.01) |
| *H04L 29/08* | (2006.01) |

(52) U.S. Cl.
CPC ........... *B60W 50/0098* (2013.01); *A61B 5/18* (2013.01); *G08B 21/06* (2013.01); *H04W 88/16* (2013.01); *B60W 2540/22* (2013.01); *B60W 2550/20* (2013.01); *H04L 67/12* (2013.01)

(58) Field of Classification Search
None
See application file for complete search history.

(56) References Cited

U.S. PATENT DOCUMENTS

| | | | |
|---|---|---|---|
| 6,154,658 A | 11/2000 | Caci | |
| 6,996,469 B2* | 2/2006 | Lau | G01C 21/3617 340/995.21 |
| 8,075,484 B2 | 12/2011 | Moore-Ede | |
| 8,935,119 B2* | 1/2015 | Yuen | G01B 21/16 702/138 |
| 8,972,175 B2 | 3/2015 | Annapureddy et al. | |
| 9,026,343 B2 | 5/2015 | Mays | |
| 2009/0016073 A1* | 1/2009 | Higgins-Luthman | B60Q 1/085 362/465 |
| 2013/0335213 A1* | 12/2013 | Sherony | G08G 1/167 340/439 |

(Continued)

FOREIGN PATENT DOCUMENTS

WO    WO-2015134372 A1    9/2015

*Primary Examiner* — Adolf Dsouza
(74) *Attorney, Agent, or Firm* — Norton Rose Fulbright US LLP (57) ABSTRACT

Electronic components may be integrated in objects used by the trucking industry, such as truck, tractor trailer, cargo, and loading bay. These objects may then communicate with each other and with a gateway device to transmit or receive data or commands. The gateway may be configured to attach to the truck, such as by securing to the truck frame or securing to an interior of the truck cab. The gateway may couple to one or more input devices, and receive sensor data through the one or more input devices. The gateway may execute steps that allow the gateway to assess a driver's condition and provide alerts and suggestions to improve the driver's safety and health.

18 Claims, 9 Drawing Sheets

(56) References Cited

U.S. PATENT DOCUMENTS

| | | | |
|---|---|---|---|
| 2014/0240132 A1 | 8/2014 | Bychkov | |
| 2014/0309849 A1* | 10/2014 | Ricci | B60Q 1/00 |
| | | | 701/33.4 |
| 2015/0160019 A1* | 6/2015 | Biswal | G01C 21/26 |
| | | | 701/1 |
| 2015/0325062 A1* | 11/2015 | Mason | G07C 5/0816 |
| | | | 701/29.3 |
| 2017/0355377 A1* | 12/2017 | Vijaya Kumar | B60W 40/08 |

* cited by examiner

DETERMINING A DRIVER CONDITION USING A VEHICLE GATEWAY

CROSS-REFERENCE TO RELATED PATENT APPLICATIONS

This application is related by subject matter to U.S. patent application Ser. No. 15/286,435 filed on Oct. 5, 2016 entitled, "Trailer Identification, Inspection, and Verification Using a Vehicle Gateway," to U.S. patent application Ser. No. 15/286,476 filed on Oct. 5, 2016 and entitled, "Cargo Geofencing using a Vehicle Gateway," to U.S. patent application Ser. No. 15/286,499 filed on Oct. 5, 2016 and entitled, "Trailer Loading using a Vehicle Gateway," to U.S. patent application Ser. No. 15/286,520 filed on Oct. 5, 2016 and entitled, "Truck Safety Zone using a Vehicle Gateway," and to U.S. patent application Ser. No. 15/286,526 filed on Oct. 5, 2016 and entitled, "Vehicle Firmware Update using a Vehicle Gateway," the disclosures of which are incorporated by reference herein.

FIELD OF THE DISCLOSURE

The instant disclosure relates to electronic devices. More specifically, portions of this disclosure relate to integration of electronic devices in the operation of vehicles.

BACKGROUND

As the value and use of information continues to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

Information handling systems have garnered ubiquitous use in certain fields, such as financial transactions, data storage, and the like. This is due, in part, to the ability of information handling systems to handle large numbers of tasks with significantly fewer errors than other techniques. Information handling systems can be designed or programmed specifically to perform certain functions, and thus take advantage of further speed advantages from this customization. However, there are certain industries and fields that have historically not modernized to take advantage of the capabilities of information handling systems, or to not fully take advantage of such systems by having specially-designed components. One such industry is the trucking industry. Tractor trailers are responsible for a significant amount of merchandise movement throughout the country and continent, and typically also a part of every merchandise's journey. The population is continuously growing, and also the demand for merchandise. Thus, the trucking industry is also continuously growing. The number of tractor trailers on the road and the number of deliveries by each tractor trailer are continuing to increase. Yet, there has been little modernization of the trucking industry.

However, lack of modernization and implementation of information handling systems has caused many problems with operation of a fleet of tractor trailers. As one example, there is little to no monitoring of truck driver health, such as enforcement of sleep requirements or monitoring of other health issues, which can result in unsafe driving and collisions involving tractor trailers. As another example, fuel efficiency is critical to profit margins of the tractor trailers, and yet there is little or no monitoring of engine operating conditions. As yet another example, the distribution of freight within a tractor trailer can impact operational efficiency and driving stability, and yet there is no optimization of freight arrangements within the tractor trailer. As a further example, the only monitoring of tractor trailers is through GPS devices with limited functionality. Thus drivers often pick up the wrong trailer in a shipping yard, which leads to lost or misdirected merchandise and lost profit.

SUMMARY

Electronic components may be integrated in objects used by the trucking industry, such as truck, trailer, cargo, and loading bay. These objects may then communicate with each other and/or with a gateway device to transmit or receive data or commands. The communications between devices may include relay of information from the objects to a remote server through the Internet. Either the gateway device or the remote server may use the relayed information to verify certain information or provide instruction to vehicle operators to improve efficiency and accuracy of the trucking industry. For example, by verifying trailers assigned to trucks have been picked up by the correct trucks, a reduction in misdirected or lost merchandise is obtained. As another example, by ensuring inspection checklists are completed, costly malfunctions may be avoided and profit margins increased. As a further example, by monitoring the health of the user, the user may feel more secure and happy with their job and thus drivers may be retained longer.

A vehicle gateway, or just "gateway," may be configured to attach to the truck, such as by securing to the truck frame or securing to an interior of the truck cab. The gateway may receive power from the vehicle power system and/or an independent power supply, such as a battery or solar cell. Although vehicle gateways are described as part of a vehicle, the gateways may be used in areas outside of the vehicle such as in loading bays, parking areas, or the like. The gateway may couple to one or more input devices to receive sensor data. The gateway may also be configured, for some of the input devices, to transmit commands to alter operation of certain components onboard or off-board the vehicle. For example, one input device may be a communications radio, such as a Wi-Fi radio, Bluetooth radio, cellular communication radio, or other short-range or long-range communication radio. Through the communications radio the gateway may receive sensor data, for example, from sensors located throughout the trailer or nearby the trailer (e.g., in range of the communications radio). For example, the sensors may be attached to the trailer. In another example, the sensors may be in nearby containers and/or in nearby vehicles. As another example, an input device may be an interface for connecting to an engine computer, such as an OBDII port. The gateway may process raw data received from the electronic components, store the raw or processed data, and/or relay the raw or processed data to a remote server.

The integration of electronic components in the trucking industry makes available new applications for these electronic components and improves operations and efficiency in the trucking industry. For example, beacon devices, or just "beacons," may be integrated with trailers and a vehicle gateway may activate the beacon to determine the trailer identification and verify the correct trailer is being picked up by the vehicle. The beacons may include a memory circuit with stored information and a communications circuit for communicating the stored information to a gateway. As another example, the vehicle gateway may communicate with biometric systems, including mobile devices such as smart watches and mobile phones, to collect information regarding driver behaviors, such as sleep patterns, to assess a condition of the driver. As a further example, electronic sensors may be integrated throughout a tractor trailer and communicate with the vehicle gateway to monitor and/or optimize loading of cargo into the tractor trailer. As yet another example, beacons may be attached to cargo containers and the beacons linked with contents of the cargo such that a vehicle gateway may determine conflicts that may exist between different cargo contents that may create a hazardous condition. As another example, vehicle gateways may communicate with other vehicle gateways to determine and/or optimize formation of vehicle platoons and provide information that ensures safety of nearby vehicles. As a further example, a vehicle gateway may monitor driving conditions and/or a planned truck route to determine when a different engine firmware may provide better fuel efficiency or other benefits and then update the engine firmware with an appropriate firmware.

The vehicle gateway may operate as a data collection device and/or a data processing device. As described throughout, the gateway may receive data from input devices that communicate with beacons, sensors, mobile devices, or other components. This data may be forwarded through, for example, cellular communications systems to cloud-based server that process the data. A driver or other user may then access a dashboard presenting the information and/or alerts based on the information through a web-based interface. Further, the driver or other user may issue commands to the vehicle gateway that are relayed to components in communications with the gateway. The commands may include, for example, remotely updating an engine firmware, changing a vehicle route, establishing new stops on the route, providing messages to a driver, or placing operating restrictions on the vehicle. Cloud-based servers may also automate certain functions by performing monitoring of the received data and sending commands to the gateway when certain conditions are satisfied. Although the gateway may communicate with cloud-based server, the gateway may also independently perform some or all of these functions. For example, a driver or user may access the gateway through a mobile device or nearby computer to access data stored on the gateway. Further, the gateway may process the data and analyze the data to determine if certain conditions are satisfied and take action, such as by transmitting alerts to the driver or another user.

According to embodiments, an information handling system may include at least one input device configured to collect information regarding habits of a driver of a vehicle. The information handling system may also include a vehicle gateway configured to attach to the vehicle and to communicate with or include the at least one input device. The vehicle gateway may be configured with hardware and/or software for collecting data from sensors throughout the vehicle and/or a driver's mobile devices, for learning driver habits from the collected data, and/or for determining a condition of the driver. For example, the vehicle gateway may be configured to perform steps including receiving information regarding actions of the driver from the at least one input device and determining a condition of the driver based, at least in part, on the received information regarding actions of the driver. As another example, the driver's past actions may be used to determine a driver's habit to use as a baseline reference, and the current actions compared with the driver's habit to determine the driver's condition. As a further example, the sensor data received through the input device may be used to determine the driver's condition. Aspects of these examples may be combined in a determination regarding the driver's condition and in a generation of alerts or recommendations for the driver.

The foregoing has outlined rather broadly certain features and technical advantages of embodiments of the present invention in order that the detailed description that follows may be better understood. Additional features and advantages will be described hereinafter that form the subject of the claims of the invention. It should be appreciated by those having ordinary skill in the art that the conception and specific embodiment disclosed may be readily utilized as a basis for modifying or designing other structures for carrying out the same or similar purposes. It should also be realized by those having ordinary skill in the art that such equivalent constructions do not depart from the spirit and scope of the invention as set forth in the appended claims. Additional features will be better understood from the following description when considered in connection with the accompanying figures. It is to be expressly understood, however, that each of the figures is provided for the purpose of illustration and description only and is not intended to limit the present invention.

BRIEF DESCRIPTION OF THE DRAWINGS

For a more complete understanding of the disclosed system and methods, reference is now made to the following descriptions taken in conjunction with the accompanying drawings.

DETAILED DESCRIPTION

As the value and use of information continues to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

Information handling systems may be adapted to provide services to vehicles, to fleets of vehicles, and/or to drivers of vehicles. Such information handling systems may be particularly useful in the trucking industry, where historically little modernization has occurred. Some hardware and software components for such information handling systems are described in further detail below. One such hardware component is a vehicle gateway that is configured to attached to a vehicle, such as a tractor pulling a trailer. The vehicle gateway may communicate with electronic components in and around the vehicle through wired and wireless communications paths. The gateway may also execute software components for processing the data, triggering alerts, making recommendations, and/or adjusting operation of the vehicle.

Figure 1:
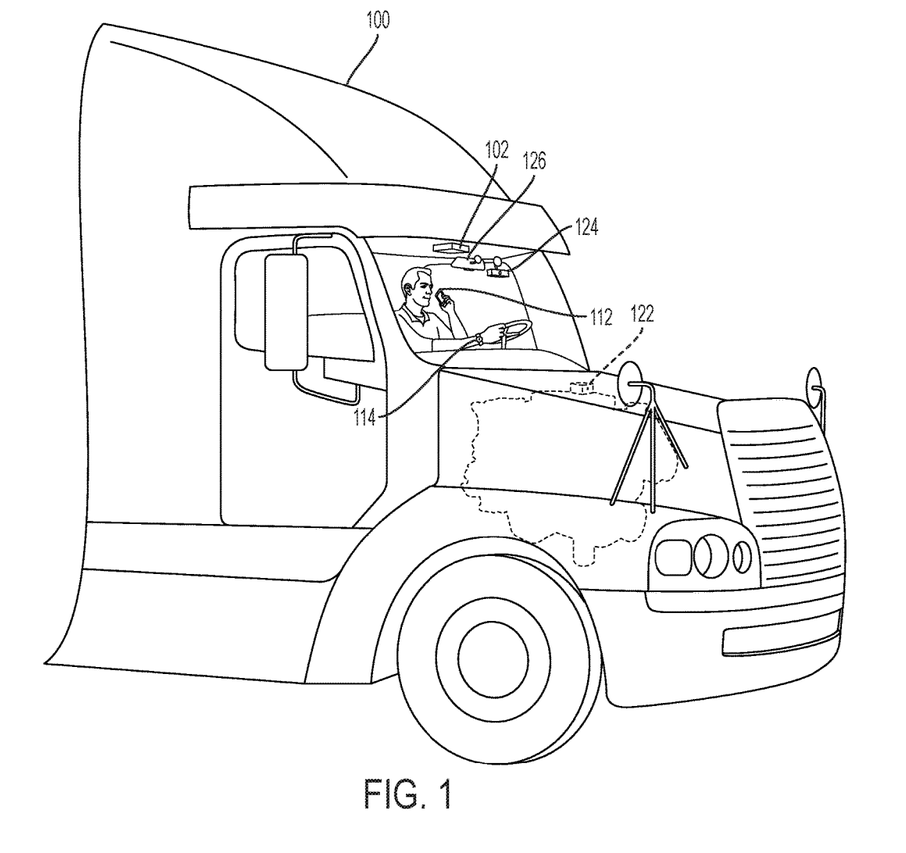
FIG. 1 is a perspective view of a vehicle illustrating an installed gateway for communicating with electronic components in or around the vehicle according to one embodiment of the disclosure.

FIG. 1 is a perspective view of a vehicle illustrating an installed gateway for communicating with electronic components in or around the vehicle according to one embodiment of the disclosure. A vehicle 100 may be a truck with tractor trailer, as shown, or another kind of vehicle, such as a car or sport-utility vehicle (SUV), or another transportation device, such as a cargo boat or aircraft. A gateway 102 may be configured to attach to and attached to the vehicle 100, such as by a screw, bolt, Velcro, adhesive, or other fixing means that affixes the gateway 102 to a component of the vehicle 100, such as a frame or an interior of a cab of the vehicle 100. In some embodiments, the gateway 102 may be a separate component inside the vehicle 100. In some embodiments, the gateway 102 may be integrated with another component attached to the vehicle 100, such as an in-dash display or radio. The gateway 102 may be connected to power or communications systems of the vehicle 100. For example, the gateway 102 may be powered from a 12 Volt direct-current (DC) bus operated by a battery in the vehicle 100. Additionally or alternatively, the gateway 102 may include a back-up or other separated power system to operate the gateway 102 when the vehicle 100 is turned off or when the vehicle 100 malfunctions.

The gateway 102 may communicate with electronic components in and around the vehicle 100 through input devices coupled to the gateway 102. For example, a driver may have a mobile phone 112, a smart watch 114, and/or other electronic devices, such as a tablet computer, a laptop computer, a television, a radio, a GPS device, etc. These mobile devices 112 and 114 may communicate with the gateway 102 through an input device such as, for example, a Bluetooth radio, a Wi-Fi radio, a near field communications (NFC) radio, or other short-range communications radio. As another example, an engine of the vehicle 100 may have an engine computer 122. The gateway 102 may include an input device configured to communicate with the engine computer 122, such as an ODBII port. The gateway 102 may be further coupled to other electronic devices, such as a road-facing camera 124 and/or an eye-tracking system 126, by either wireless or wired connections similar to that described in the examples above. The eye-tracking system 126 may be used to monitor eye movement of a driver, which can provide information regarding, for example, the driver's alertness.

Figure 2:
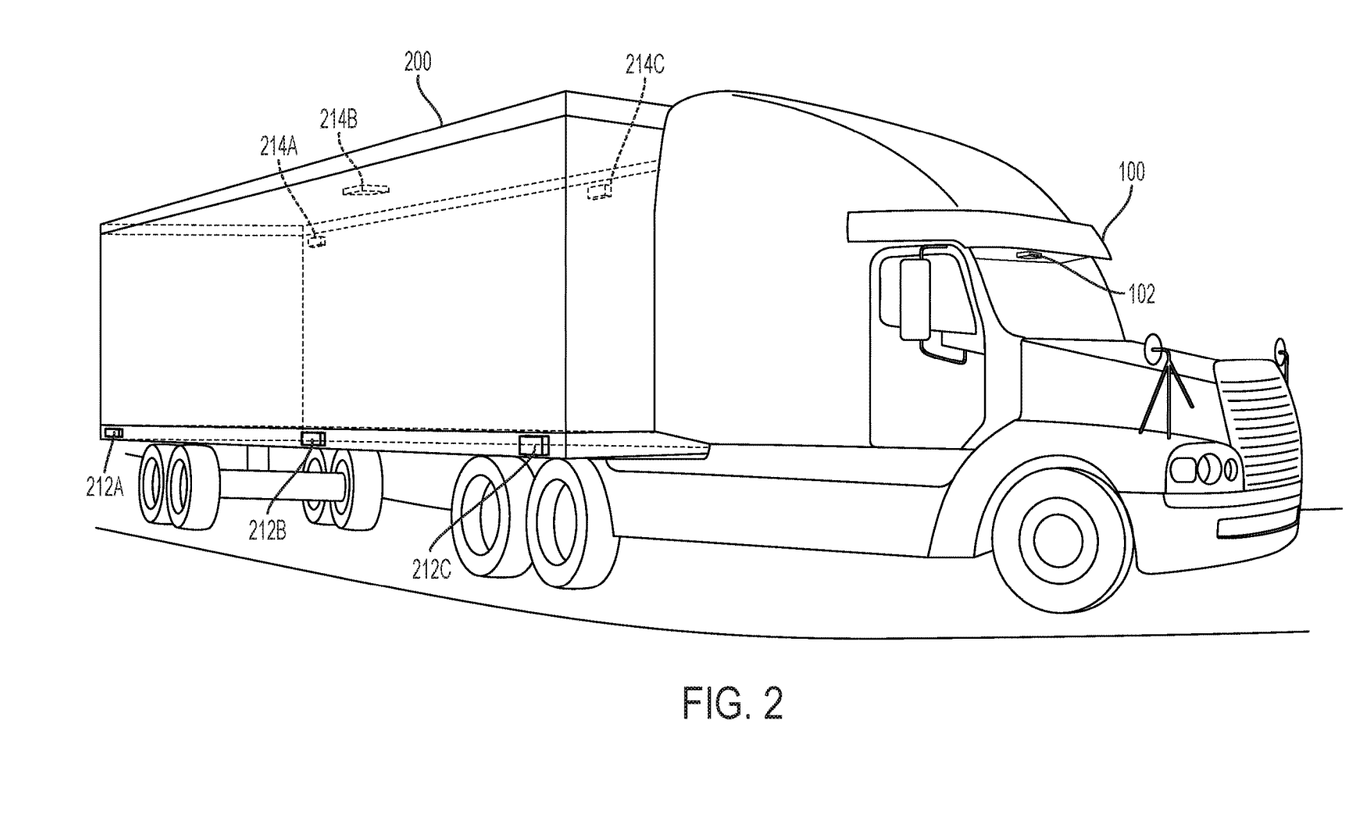
FIG. 2 is a perspective view of a vehicle illustrating an installed gateway for communicating with sensors in and around a tractor trailer attached to the vehicle according to one embodiment of the disclosure.
Figure 3:
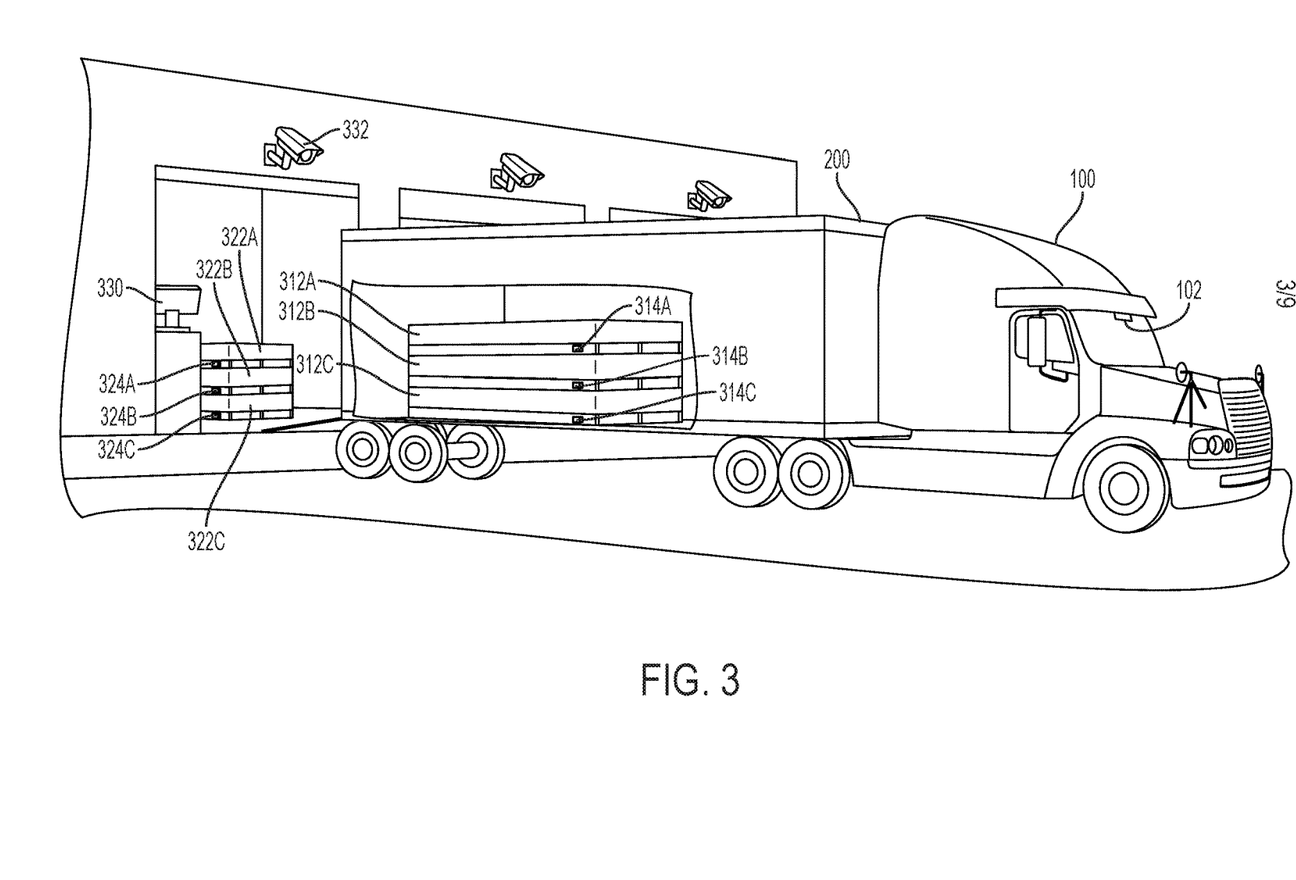
FIG. 3 is a perspective view of a vehicle illustrating an installed gateway for communicating with electronic components in and around the vehicle and in and around a loading bay according to one embodiment of the disclosure.
Figure 4:
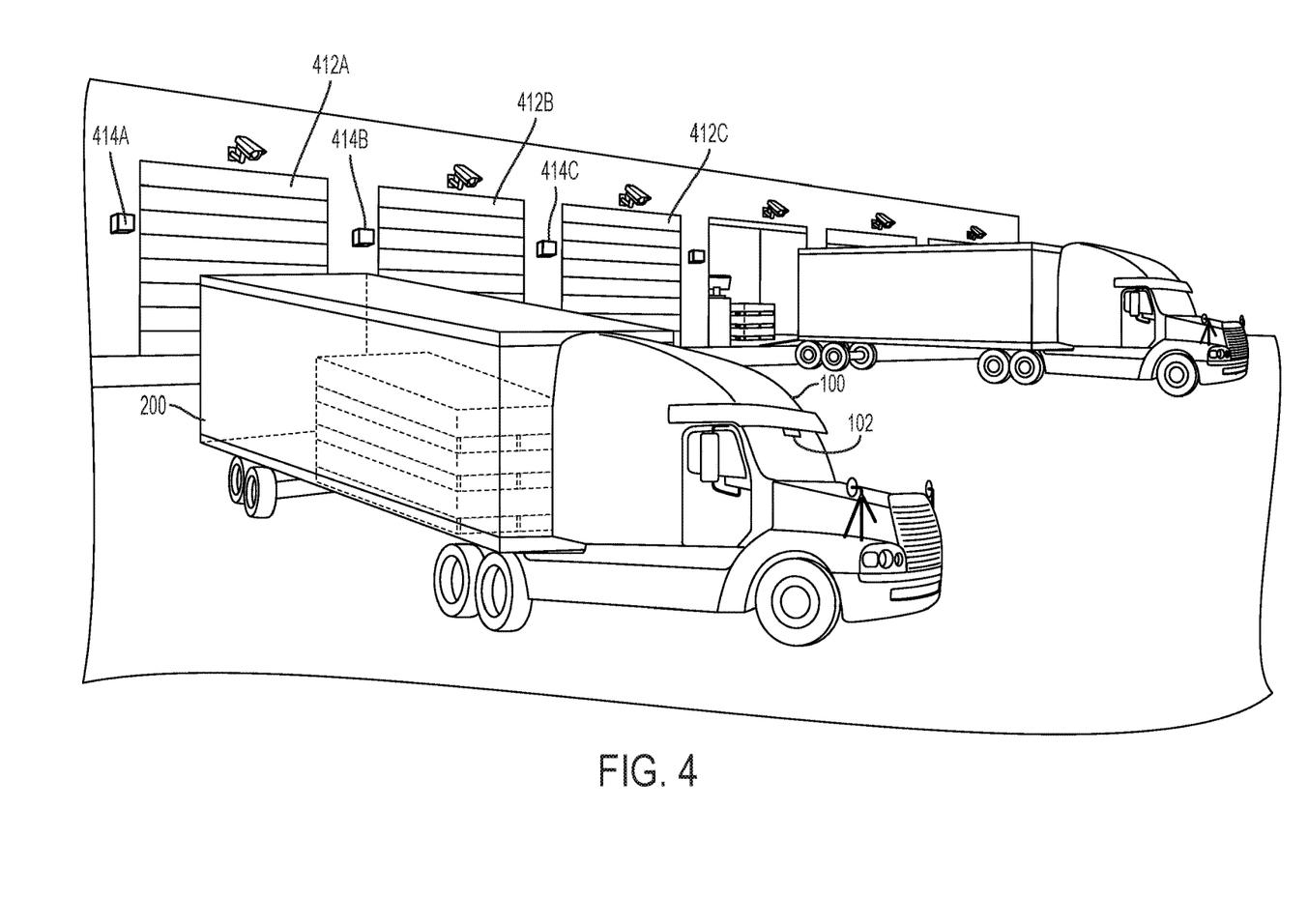
FIG. 4 is a perspective view of a vehicle illustrating an installed gateway for communicating with electronic components in cargo and around a loading bay or other nearby vehicles according to one embodiment of the disclosure.

FIG. 1 shows one configuration of wireless devices that includes user mobile devices 112 and 114, the engine computer 122, the camera 124, and the tracking system 126. However, any combination of electronic devices may be used in combination with the vehicle gateway 102 of embodiments. For example, although FIG. 1 illustrates electronic devices in and around the truck cab, electronic devices may be anywhere in communications range. For example, devices may be in an attached or nearby truck trailer, as shown in FIG. 2, wherein a nearby truck trailer may be a truck trailer within short-range communications range of the vehicle 100. Communications with nearby beacons and gateways may allow, for example, a gateway to identify locations of missing or stolen trailers or cargo when passing within short-range communications range. Further, the vehicle gateway 102 may communicate with stationary gateways and electronic devices, such as beacons, sensors, devices, and gateways in a loading bay as shown in FIG. 3 and FIG. 4. The gateway 102 may also communicate with gateways on other vehicles. For example, a plurality of gateways installed on a plurality of vehicles may communicate with each other to form a mesh network allowing one of the gateways to communicate through other gateways when its long-range communications radio is not functioning correctly.

FIG. 2 is a perspective view of a vehicle illustrating an installed gateway for communicating with sensors in and around a tractor trailer attached to the vehicle according to one embodiment of the disclosure. The gateway 102 may be coupled to or integrated with an input device, such as a low-power RF radio for wireless communications, to communicate with electronic devices 212A, 212B, and 212C attached to a tractor trailer 200. The devices 212A-C may be, for example, sensors (e.g., GPS receivers) or cameras. The devices 212A-C may report loading of the cargo in the trailer or air pressure in tires of the trailer. The same input device may also be used to communicate with electronic devices 214A-C inside the tractor trailer. The devices 214A-C may be beacons attached to cargo that provide information about cargo carried by the tractor trailer or cameras mounted in the interior of the trailer. Example uses of devices attached to the frame and inside the trailer are provided below. The gateway 102 may collect information from the devices 212A-C and 214A-C. The information may be processed by the gateway 102 and used, for example, to assist in arranging cargo in the trailer and in verifying loading of correct cargo in the trailer.

FIG. 3 is a perspective view of a vehicle illustrating an installed gateway for communicating with electronic components in and around the vehicle and in and around a loading bay according to one embodiment of the disclosure. The gateway 102 may communicate with electronic devices outside the vehicle, such as in a loading bay, to facilitate management of cargo in the trailer. For example, cargo pallets 312A, 312B, and 312C inside of the trailer 200 may each have an attached electronic device 314A, 314B, and 314C, respectively, such as a beacon. The beacons 314A-C may transmit cargo identification information that includes an identifier for the attached cargo pallet. The beacon 314A-C may also transmit other information, such as contents of the cargo pallet. In some embodiments, the beacons 314A-C may be active devices that are continuously transmitting data. In other embodiments, the beacons 314A-C may be passive devices that only transmit information when interrogated, similar to RFID tags. Additional cargo pallets 322A, 322B, and 322C may be located inside the loading bay, with attached beacons 324A, 324B, and 324C, respectively. The beacons 324A-C may communicate with the gateway 102 directly. The beacons 324A-C may also communicate with a second gateway 330 inside the loading bay, which may relay information to the gateway 102. Additional electronic devices, inside or outside the trailer 200, may provide further information, such as to verify correct loading of cargo. For example, cameras 332 may capture images or video of the loading of cargo pallets 312A-C and/or 322A-C to provide visual confirmation to verify information from the beacons 322A-C and 324A-C. For example, a gateway 102 may determine if an approximate size of the pallet 312A matches a size of the cargo contents indicated by beacon 322A.

FIG. 4 is a perspective view of a vehicle illustrating an installed gateway for communicating with electronic components in cargo and around a loading bay or other nearby vehicles according to one embodiment of the disclosure. When a vehicle is moving, some electronic devices may enter and exit communications range of the gateway 102. For example, as a tractor trailer drives through a set of loading bays, the gateway 102 may establish communication with each of the electronic devices 414A, 414B, and 414C associated with loading bays 412A, 412B, and 412C, respectively. The gateway 102 may communicate with the electronic devices 414A-C to determine a correct loading bay. The gateway 102 may also communicate with the electronic devices 414A-C to determine if any of the loading bays 412A-C contain cargo that could be potentially hazardous if in close proximity to cargo carried in the trailer. As another example, a vehicle may drive through the loading bays with a gateway 102 to inventory the cargo in the loading bays 412A-C. This would allow for periodic updating of the location of cargo and the ability to find misplaced cargo by driving a vehicle through the loading bay. Alternatively or additionally, the tractor trailers may scan for missing cargo as they drive through the loading bay to pick up or drop-off cargo.

Figure 5:
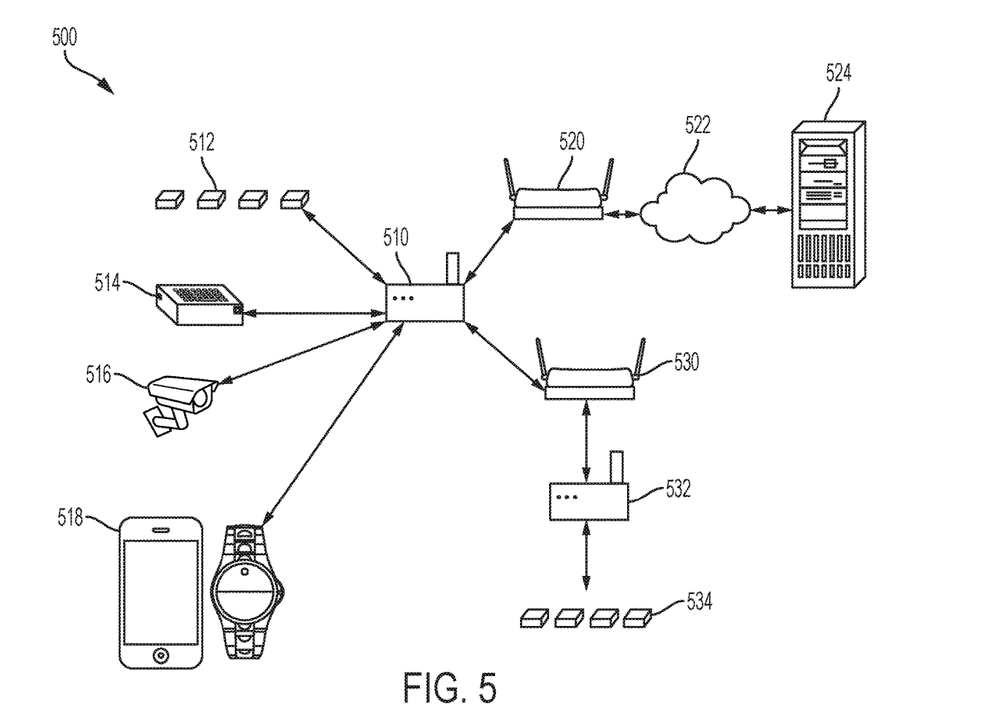
FIG. 5 is a block diagram illustrating communications paths around a vehicle gateway for communicating with electronic components according to one embodiment of the disclosure.

As described in the examples above, many combinations of electronic devices such as shown in FIG. 1, FIG. 2, FIG. 3, and FIG. 4 may be configured to operate with a vehicle gateway. An illustration of communications between the electronic devices is described in FIG. 5 without reference to any particular application. FIG. 5 is a block diagram illustrating communications paths around a vehicle gateway for communicating with electronic components according to one embodiment of the disclosure. A gateway 510 may be coupled to and/or include various input devices to accommodate communication with a variety of devices in different configurations. The gateway 510 may be programmed, such as through firmware or software, to perform a number of different functions involving the various electronic devices. Although certain trucking examples are described in FIG. 1, FIG. 2, FIG. 3, FIG. 4, and the examples below, the gateway 510 may be configured to perform many other functions. For example, rather than using the gateway 510 on a truck for cargo management, the gateway 510 may be installed in a passenger vehicle and used to assist a driver on a cross-country trip. Further, the gateway 510 need not be limited to land vehicles, but may also be used in other configurations, such as on boats and aircraft for tracking cargo.

The gateway 510 may be coupled to and/or include input devices for communicating with local electronic devices that are in or near the vehicle. For example, the gateway 510 may be configured with wireless or wired communication input devices to receive data from vehicle sensors 512, an engine computer 514, cameras 516, and/or mobile devices 518. The input devices configured to communicate with the devices 512, 514, 516, and/or 518 may include wired communications interfaces, such as Ethernet, OBDII, serial, or parallel interfaces, and/or wireless communications interfaces, such as Wi-Fi, Bluetooth, ZigBee, RFID, or NFC.

The gateway 510 may also be coupled to input devices, such as modem devices, for communicating with electronic devices away from the vehicle. For example, the gateway 510 may be coupled to a long-range communications modem 520 for communicating over a network 522, such as the Internet, with remote servers 524. The remote servers 524 may offer storage and/or processing capabilities that enhance the function of the gateway 510. As another example, the gateway 510 may be coupled to and/or include a short-range communications modem 530 for communicating with a second gateway 532. The second gateway 532 may be attached to a second vehicle and be configured to communicate with electronic devices 534 in or near the second vehicle. The gateway 510 may have access to raw data from the electronic devices 534 and/or receive processed data from the second gateway 532.

The vehicle gateway may be used to track a driver's behavior and determine a driver's condition. Commercial drivers often work odd hours. Long runs of time while requiring close attention to many variables can tire a driver. This may lead to retention difficulty of drivers, and greater physical and mental health issues for drivers. Further, tired drivers may be more likely to make mistakes that may cause vehicle collisions or that may cause a driver to move wrong cargo to a wrong location. The vehicle gateway may be configured to provide feedback to a driver to assist the driver in managing their work to prevent mistakes and improve mental and physical health. For example, the vehicle gateway may monitor driver awareness (e.g., through in-cab eye-tracking, head position detection) and driver heart rate (e.g., through a heart rate sensor in a driver's smart watch or a pulse sensor integrated with the steering wheel). As another example, the vehicle gateway may monitor driver driving behavior (e.g., through lane departure systems or through speed variations). As another example, the vehicle gateway may monitor driver driving time (e.g., through monitoring opening and closing of doors). The vehicle gateway may determine if a driver is sufficiently rested or otherwise in good condition to operate a vehicle. If the driver's behavior indicates certain deficiencies in their wellness or fitness to operate the vehicle, the vehicle gateway may cause alerts to be presented (e.g., through a visual display or audible announcement) to the driver with recommendations for correcting the efficiencies.

Figure 6:
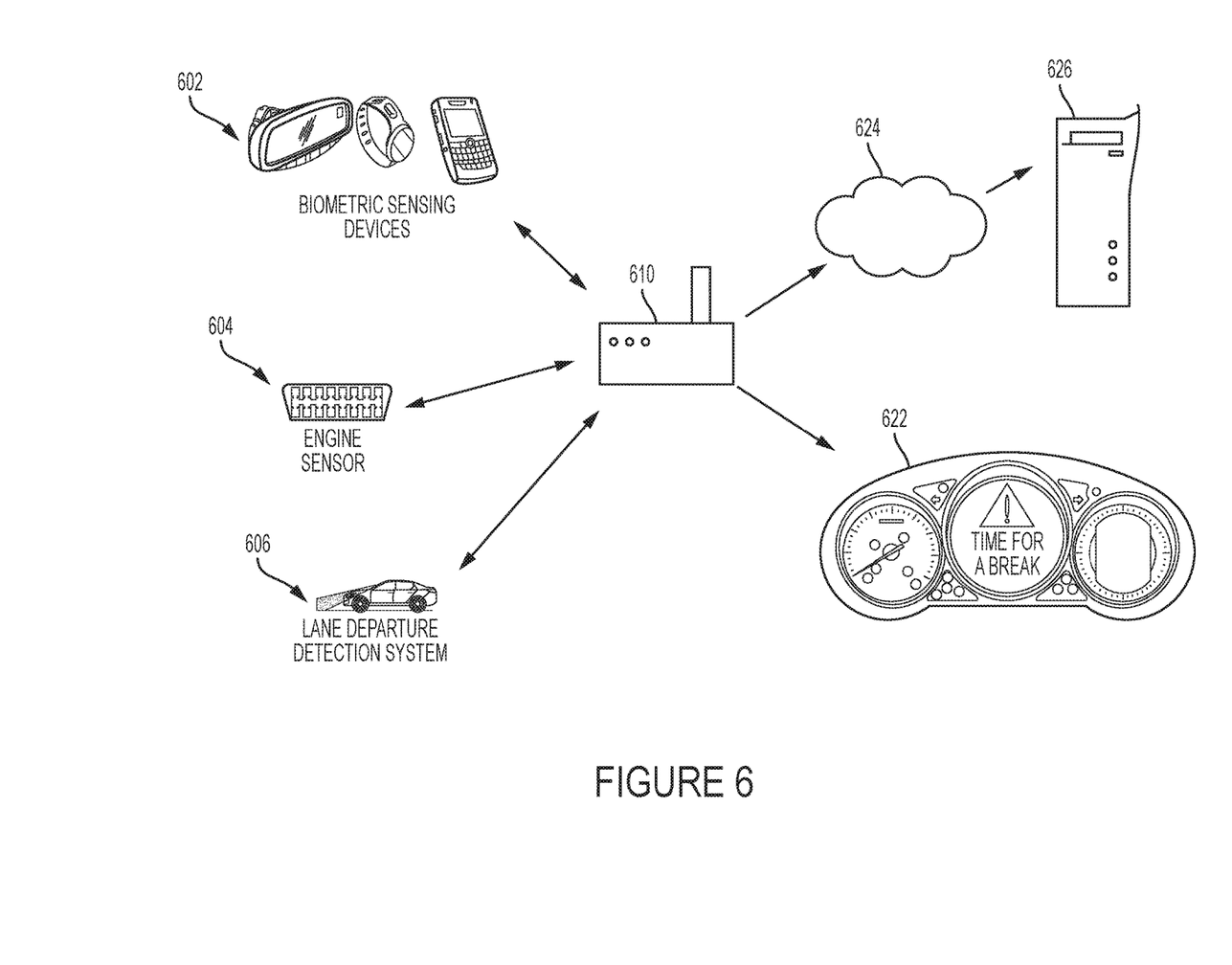
FIG. 6 is a block diagram illustrating example operation of a vehicle gateway with other devices for monitoring a driver's condition according to one embodiment of the disclosure.

Data may be collected by the vehicle gateway from one or more sources through one or more input devices. The data may be used for determining a condition of the driver, and providing recommendations to the driver. FIG. 6 is a block diagram illustrating example operation of a vehicle gateway with other devices for monitoring a driver's condition according to one embodiment of the disclosure. A vehicle gateway 610 may receive information from biometric sensing devices, such as an eye-watching system, camera (e.g., to view head or body position and movement), pulse sensor, microphone (e.g., to listen for breathing, depth and speed of respiration, or to listen to driver answers to voice prompts), a mobile phone, and/or a smart watch. The vehicle gateway 610 may communicate with such devices through an input device such as a short-range communication radio, such as Bluetooth or Wi-Fi, or a wired connection. Further, user devices such as smartwatches or mobile phones may be used to collect information such as where the driver located around the truck, determine if the driver is within a certain proximity, determine if the driver is sleeping in the truck, or determine how well the driver slept. The vehicle gateway 610 may also or alternatively receive information from an engine computer 604, such as fuel level, gear shifting efficiency, and/or speed. The vehicle gateway 610 may communicate with the engine computer through an input device such as an OBDII port. The vehicle gateway 610 may also or alternatively receive information from a lane departure detection system 606, such as through an input device such as a wired communications line.

The vehicle gateway 610 may use the collected driver information to determine a condition of the driver. The driver evaluation may be performed locally on the vehicle gateway 610. The information and/or results of the determination may be transmitted through a wide area network (WAN) connection 624, such as the Internet, to a remote server 626. The remote server 626 may store the information or perform analysis on the information. In some embodiments, the remote server 626 may transmit a determination regarding the driver or other driver information back to the vehicle gateway 610. The determined driver condition may be pushed from the vehicle gateway 610 to a display, such as a digital display integrated with a dashboard 622, or a user's mobile device. Software on the vehicle gateway 610 may be configured to operate in collaboration with hardware, such as the wearables and truck sensors, to aid in improving overall safety, health, and/or efficiency of drivers.

Figure 7:
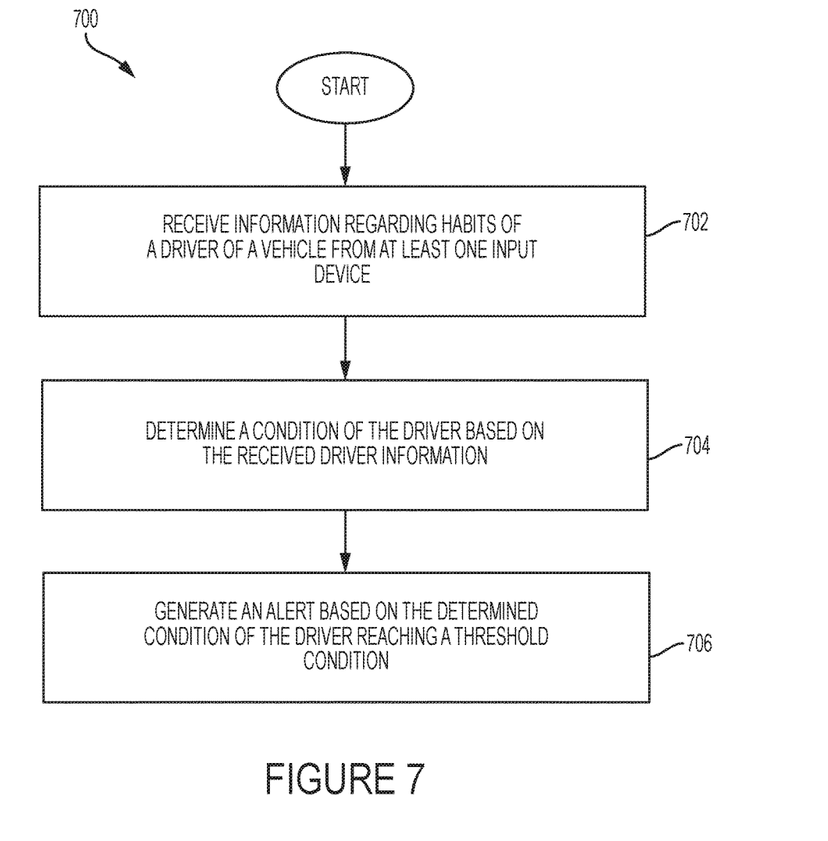
FIG. 7 is a flow chart illustrating an example method for monitoring a condition of a driver with a vehicle gateway according to one embodiment of the disclosure.

One example method for execution by a vehicle gateway in determining a driver's condition is shown in FIG. 7. FIG. 7 is a flow chart illustrating an example method for monitoring a condition of a driver with a vehicle gateway according to one embodiment of the disclosure. A method 700 may begin at block 702 with receiving information regarding habits of a driver of a vehicle from at least one input device. Information regarding habits may be determined based on past actions of the driver indicated by data received from input devices coupled to the gateway. For example, driving information regarding gear shifting may be received from an engine computer, driver information regarding lane departures may be received from a lane departure detection system, driver information regarding awareness may be received from an eye-tracking system, driver information regarding sleep health may be received from a user's mobile device, driver information regarding heart rate may be received from a user's smartwatch, and/or driver information regarding a driver's work schedule may be received from an engine computer or the driver's mobile device. At block 704, a condition of the driver may be determined based on the received driver information of block 702. The driver condition may be determined by comparing current sensor data, a current driver action, and/or recent driver actions with the driver's habits determined at block 702. For example, block 704 may include determining an amount of time the driver slept over a recent time period and then determining if the sleep time is over a threshold amount that would indicate that the driver has received sufficient rest. The threshold amount may be determined, in part, based on the driver's habits, such as average number of hours of sleep per night. At block 706, an alert may be generated when the determined condition of the driver indicates a problem, such as when a threshold condition is reached. The alert may be presented to the user through their mobile device and/or a display, such as a dashboard in the car. The alert may also or alternatively be transmitted to a remote server, which may store the determination for future reference and/or alert the driver to the problem, and/or alert the driver's supervisor to the problem.

Figure 8:
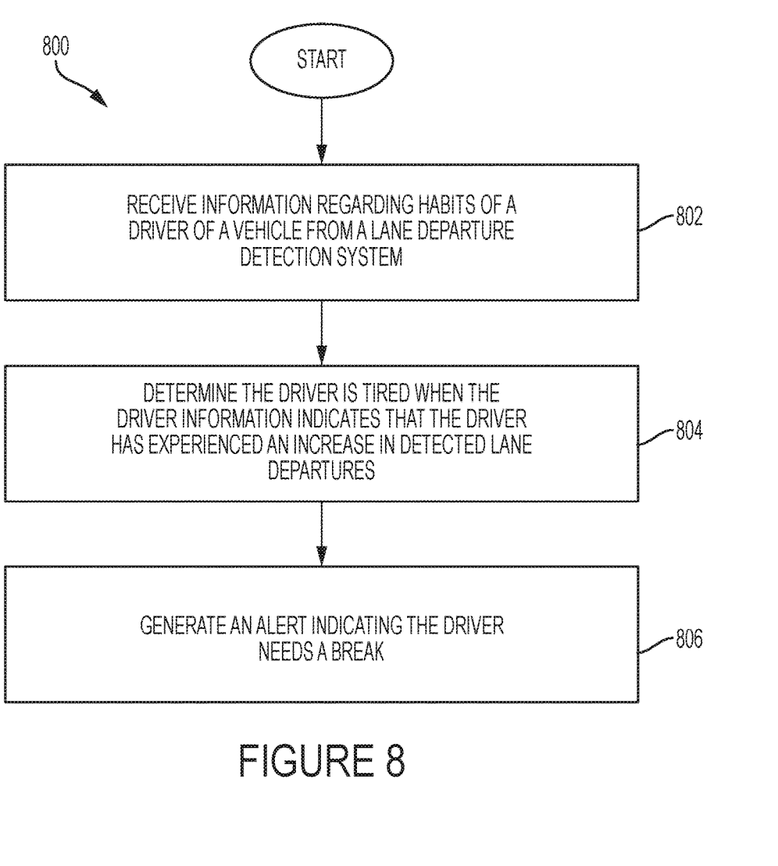
FIG. 8 is a flow chart illustrating an example method for determining when a driver needs a break based on driving behavior according to one embodiment of the disclosure.

In one embodiment, the driver condition being detected may be driver fatigue indicated by an increase in lane departures. Drifting in and out of lanes may indicate a driver that is fatigued or occasionally sleeping during driving. One method for detecting this behavior with a vehicle gateway is described with reference to FIG. 8. FIG. 8 is a flow chart illustrating an example method for determining when a driver needs a break based on driving behavior according to one embodiment of the disclosure. A method may begin at block 802 with receiving information regarding habits of a driver from a lane departure detection system. The received information may be an indication of an average number of lane departures by the driver over a particular historical time period. Some lane departures may be acceptable due to error on the lane detection system or due to forgetting to turn on a signal when changing lanes. At block 804, the vehicle gateway may determine if the driver is fatigued when the driver information from block 802 has experienced an increase in detected lane departures. For example, the vehicle gateway may determine an average number of lane departures for a driver based on historical data and then determine if a recent number of departures exceeds the average number by more than a threshold amount. Regardless of the average number, the driver may be determined as fatigued if the recent number of departures exceeds a certain predetermined threshold. At block 806, the vehicle gateway generates an alert indicating the driver is fatigued and needs a break. For example, an alert may be displayed to the driver suggesting the driver stop operating the vehicle. Referring back to FIG. 6, an alert may be displayed on dashboard 622. As another example, an alert may be transmitted to a remote server for a supervisor to review. As a further example, the vehicle gateway may shut down vehicle components, such as a radio or the engine. As still a further example, the vehicle gateway may limit the maximum speed of the vehicle until the driver takes a break and obtains sufficient rest. In some embodiments, the method 800 may also include a further step of taking an action to inhibit driver operation. For example, when driver fatigue is detected the gateway may place an upper speed limit on the vehicle or may alter the driver's route to enter a nearby rest stop or hotel.

Figure 9:
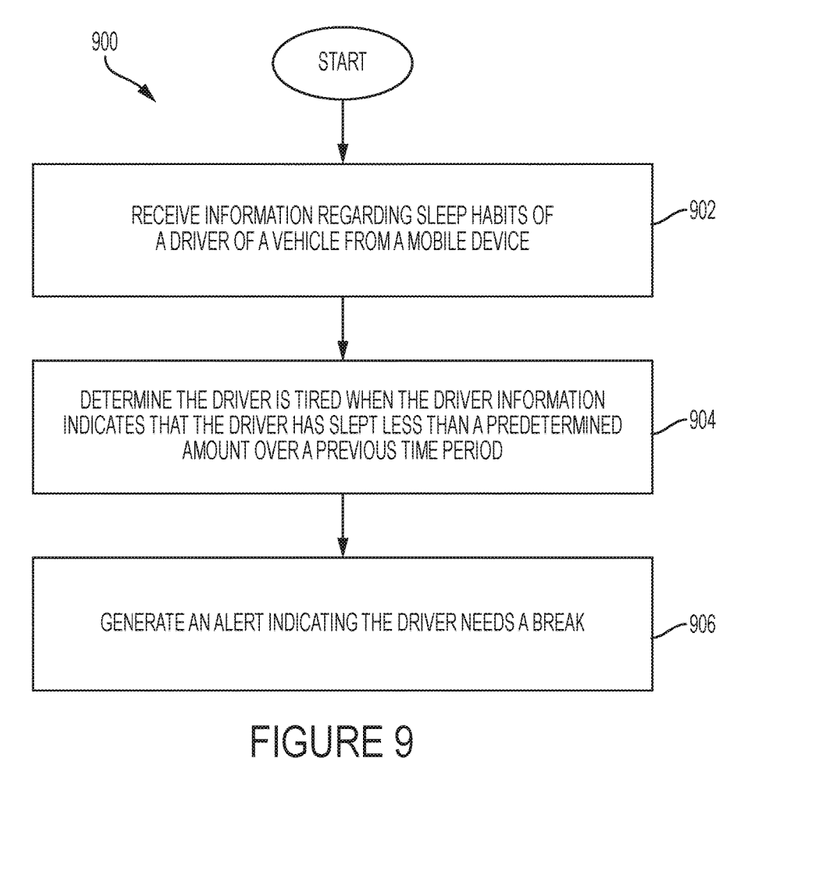
FIG. 9 is a flow chart illustrating an example method for determining when a driver needs a break based on sleeping behavior according to one embodiment of the disclosure.

In one embodiment, the driver condition being monitored may be fatigue indicated by insufficient sleep. A user's mobile device may be used to monitor a driver's biometric conditions. For example, a smart watch may be used to determine a user's sleep habits and an amount of time sleeping. As another example, a smart watch may include a heart rate monitor to determine if a driver's heart rate is depressed, indicating fatigue. FIG. 9 is a flow chart illustrating an example method for determining when a driver needs a break based on sleeping behavior according to one embodiment of the disclosure. A method 900 may begin at block 902 with a vehicle gateway receiving information regarding sleep habits of a driver of a vehicle from the driver's mobile device and/or other sensors through the input devices (e.g., reports of engine operating times from the engine computer, reports of user's head position from a camera). The habits may include, for example, the driver's average number of hours of sleep in a night and/or average number of hours driven without a break over the past month. At block 904, the vehicle gateway determines if the driver is fatigued based on the driver information received from block 902. The fatigued determination may be based on determining that the driver has slept less than a predetermined amount over a recent time period, such as 48 hours, in which the predetermined amount is selected based on the driver's habits determined at block 902.

More generally, the vehicle gateway may learn a driver's habits and may use the learned behaviors to determine whether the driver is safe to operate a vehicle or not. For example, using data gathered from a vehicle (e.g., GPS, fuel level, etc.), and adding data gathered from the driver's wearable devices, the vehicle gateway may deliver a route plan or daily plan that allows for awareness and opportunity to have the driver exercise, get nutrients, and sleep more efficiently with regards to refueling, sleeping, exercising, maintenance, and the like. The vehicle gateway may provide a combination of hardware and software for recording analyzing, and transmitting driver information. When information from multiple drivers is combined, a routing map may be generated for a fleet of vehicles and drivers based on the learned driver habits. When the driver is not in a condition for operating the vehicle, the vehicle gateway may refuse to unlock doors to the vehicle or refuse to allow release of a parking brake of the vehicle.

Although determining user habits is described above, a user's condition may also be assessed from only recent data received from the input devices. For example, an immediate condition of the vehicle or the driver may be used to determine the driver's condition. When a user's head position captured by a camera is down for more than two consecutive seconds the driver may be determined to be fatigued. As another example, information regarding recent operation may be compared to a supervisor's expected norms or regulated norms. Some regulations may specify that a driver may not operate a vehicle for more than eight straight hours, and the engine uptime determined from an engine computer or user's mobile device may indicate when the eight-hour regulation is exceeded. As yet another example, information regarding recent operation by the driver may be compared to averages obtained from a fleet of vehicles. An average number of lane departures may be determined for any ten-minute interval across a fleet of vehicles, and when a driver has more lane departures than that average number, the driver may be determined to be fatigued. Although separate examples are provided, in some embodiments the vehicle gateway may combine different types of thresholds and apply different types of thresholds to different inputs in determining a driver's condition.

The schematic flow chart diagrams of FIG. 7, FIG. 8, and FIG. 9 are generally set forth as a logical flow chart diagram. As such, the depicted order and labeled steps are indicative of aspects of the disclosed method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagram, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The operations described above as performed by a gateway, beacon, or electronic device may be performed by any circuit configured to perform the described operations. Such a circuit may be an integrated circuit (IC) constructed on a semiconductor substrate and include logic circuitry, such as transistors configured as logic gates, and memory circuitry, such as transistors and capacitors configured as dynamic random access memory (DRAM), electronically programmable read-only memory (EPROM), or other memory devices. The logic circuitry may be configured through hard-wire connections or through programming by instructions contained in firmware. Further, the logic circuitry may be configured as a general purpose processor capable of executing instructions contained in software. If implemented in firmware and/or software, functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise random access memory (RAM), read-only memory (ROM), electrically-erasable programmable read-only memory (EEPROM), compact disc read-only memory (CD-ROM) or other optical disk storage, magnetic disk storage or other magnetic storage devices, or any other medium that can be used to store desired program code in the form of instructions or data structures and that can be accessed by a computer. Disk and disc includes compact discs (CD), laser discs, optical discs, digital versatile discs (DVD), floppy disks and Blu-ray discs. Generally, disks reproduce data magnetically, and discs reproduce data optically. Combinations of the above should also be included within the scope of computer-readable media.

In addition to storage on computer readable medium, instructions and/or data may be provided as signals on transmission media included in a communication apparatus.

For example, a communication apparatus may include a transceiver having signals indicative of instructions and data. The instructions and data are configured to cause one or more processors to implement the functions outlined in the claims.

Although the present disclosure and certain representative advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. For example, although processors are described as components in gateways, beacons, mobile devices, or electronic devices, aspects of the invention may be implemented on different kinds of processors, such as graphics processing units (GPUs), central processing units (CPUs), and digital signal processors (DSPs). As another example, although processing of certain kinds of data may be described in example embodiments, other kinds or types of data may be processed through the methods and devices described above. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. An information handling system, comprising:
   at least one input device configured to collect information regarding actions of a driver of a vehicle in operating the vehicle;
   a gateway configured to attach to the vehicle and to communicate with the at least one input device, wherein the gateway is configured to perform steps comprising:
      receiving the information regarding actions of the driver from the at least one input device;
      determining a driver's habit as a baseline reference based on a first portion of the received information regarding actions of the driver;
      determining a condition of the driver based, at least in part, on a second portion of the received information regarding actions of the driver in operating the vehicle by comparing the second portion of the received information with the baseline reference; and
      disabling certain vehicle functionality when the condition of the driver indicates the driver is fatigued compared to the baseline reference for the driver.

2. The information handling system of claim 1, wherein the at least one input device comprises a communications radio configured to communicate with a mobile device, wherein the mobile device collects the information regarding actions of the driver, and wherein the gateway receives the information regarding the actions of the driver through the communications radio.

3. The information handling system of claim 2, wherein the communications radio is integrated with the gateway.

4. The information handling system of claim 2, wherein the at least one input device comprises an interface to a biometric sensing device configured to collect at least one of heart rate information, pulse information, head position information, body position information, sleep schedule information, and eye tracking information.

5. The information handling system of claim 1, wherein the at least one input device comprises an interface to an engine computer configured to collect at least one of fuel level, gear shifting efficiency, and speed.

6. The information handling system of claim 1, wherein the gateway is further configured to generate an alert for the driver based, at least in part, on the determined condition of the driver and to cause the alert to be presented to the driver.

7. The information handling system of claim 6, wherein the gateway is configured to generate an alert for the driver to take a break based, at least in part, on the determined condition of the driver indicating the driver is fatigued.

8. The information handling system of claim 1, wherein the at least one input device comprises an interface to a lane departure detection system, and wherein the gateway is configured to determine that the condition of the driver is fatigued when the received information collected by the lane departure detection system indicates an increase in detected lane departures compared to an average number of lane departures of the determined habits of the driver.

9. The information handling system of claim 1, wherein the at least one input device comprises a communications radio configured to communicate with a smart watch, and wherein the gateway is configured to determine that the condition of the driver is fatigued when the received information collected by the smart watch indicates the driver has slept less than a threshold amount over a recent time period, wherein the threshold amount is based, at least in part, on the determined habits of the driver.

10. The information handling system of claim 1, wherein the gateway is configured to perform steps comprising limit a maximum speed of the vehicle when the condition of the driver indicates the driver is fatigued.

11. The information handling system of claim 1, wherein the gateway is configured to perform steps comprising:
   transmitting an alert that the driver is fatigued to a remote server; and
   altering a driver's route to enter a nearby rest location.

12. A method, comprising:
   receiving, by a vehicle gateway, the information regarding actions of a driver in operating the vehicle;
   determining, by the vehicle gateway, a driver's habit as a baseline reference based on a first portion of the received information regarding actions of the driver;
   determining, by the vehicle gateway, a condition of the driver based, at least in part, on a second portion of the received information regarding actions of the driver in operating the vehicle by comparing the second portion of the received information with the baseline reference; and
   disabling, by the vehicle gateway, certain vehicle functionality when the condition of the driver indicates the driver is fatigued compared to the baseline reference for the driver.

13. The method of claim 12, wherein the received information comprises biometric sensor data comprising at least one of heart rate information, pulse information, body position information, head position information, sleep schedule information, and eye tracking information.

14. The method of claim 12, wherein the received information comprises engine data comprising at lead one of fuel level, gear shifting efficiency, and speed.

15. The method of claim 12, further comprising generating an alert for the driver based, at least in part, on the determined condition of the driver; and causing the alert to be displayed to the driver.

16. The method of claim 15, wherein the alert is generated based on the determined condition indicating the driver is fatigued.

17. The method of claim 12, wherein the step of determining the condition comprises determining that the condition of the driver is fatigued when the received information regarding actions of the driver indicates an increase in detected lane departures from the determined habits of the driver.

18. A computer program product comprising a non-transitory computer readable medium comprising code to execute steps on a vehicle gateway, wherein the steps comprise:
- receiving, by a vehicle gateway, the information regarding actions of a driver in operating the vehicle;
- determining habits of the driver based, at least in part, on the received information regarding actions of the driver in operating the vehicle;
- determining, by the vehicle gateway, a condition of the driver by comparing a recent portion of the received information regarding actions of the driver with the determined habits of the driver, wherein the determined condition indicates whether the driver is fatigued; and
- disabling certain vehicle functionality when the determined condition of the driver indicates the driver is fatigued in comparison to the baseline reference.

* * * * *